United States Patent [19]
Keller et al.

[11] Patent Number: 5,219,498
[45] Date of Patent: Jun. 15, 1993

[54] PROCESS FOR CONTROLLING CURING AND THERMOFORMING OF RESINS AND COMPOSITES

[76] Inventors: L. Brian Keller, 11230 Occidental Rd., Sebastopol, Calif. 95472; Arturo A. Castillo, 1003 Broadmoor Ave., La Puente, Calif. 91744

[21] Appl. No.: 790,442

[22] Filed: Nov. 12, 1991

[51] Int. Cl.$^5$ .................. B29C 35/02; B29C 51/28; B29C 51/46
[52] U.S. Cl. .................. 264/40.2; 264/40.1; 264/40.6; 156/64; 425/135; 425/143; 364/476; 324/663
[58] Field of Search .................. 264/40.2, 40.1, 40.6; 425/135, 143; 364/469, 473, 476, 477; 324/663; 156/64

[56] References Cited

U.S. PATENT DOCUMENTS

| | | | |
|---|---|---|---|
| 4,373,092 | 2/1983 | Zsolnay | 264/40.3 |
| 4,399,100 | 8/1983 | Zsolnay | 374/53 |
| 4,510,103 | 4/1985 | Yamaguchi et al. | 264/40.2 |
| 4,515,545 | 5/1985 | Hinrichs et al. | 425/143 |
| 4,551,807 | 11/1985 | Hsich et al. | 425/30 |
| 4,773,021 | 9/1988 | Harris et al. | 425/143 |
| 4,868,769 | 9/1989 | Persson | 264/40.1 |
| 5,032,525 | 7/1991 | Lee et al. | 264/40.3 |

OTHER PUBLICATIONS

Keller, L. B. and Castillo, A., "Real Time In-Situ Dielectric Monitoring of Advanced Composites Curing Processes", Final Report, DARPA SBIR Contract DAAH01-89-C-0348, 1987.

*Primary Examiner*—Jan H. Silbaugh
*Assistant Examiner*—Catherine Timm

[57] ABSTRACT

Composite material consisting of reinforcing fibers are impregnated with polymeric matrices which may contain fillers and are then cured or thermoformed in a heating system such as an autoclave, press or oven. As the curing or thermoforming process proceeds, dielectric detection is employed to closely monitor critical process events such as the release of volatiles, chemical reactions such as cross linking, melting and solidification. Curves are generated by plotting factors of the dielectric loss of the polymer matrix versus time during the process, and these curves have a distinctive shape or signature that is characteristic of the particular polymer matrix being processed. These distinctive features or signatures have been found to correlate with critical process events, and these features are stored in a computer. During a cure cycle, the computer actuates the controls of the heating system so that the appropriate process actions or modifications will occur at the optimum time. The process controls are thereby adapted to produce an optimized, high quality product which is fairly independent of variations in raw material, preprocessing, tooling and the heating equipment.

21 Claims, 3 Drawing Sheets

PROCESS FOR CONTROLLING CURING AND THERMOFORMING OF RESINS AND COMPOSITES

BACKGROUND OF THE INVENTION

This invention was made, in part, under a contract from the Defense Advanced Projects Agency (DoD), contract no. DAAH01-89-C-0348.

This invention relates to a new and improved process and apparatus for curing composites of polymeric resin impregnated fabric or fibrous reinforcement, the resin possibly containing fillers such as carbon black, graphite, mineral fillers, and the like. Typical fabrics and other fibrous reinforcements contemplated by this invention include those produced from graphite, carbon, glass fiber, fiberglass, ceramics, quartz, SiC, aramid, metal fibers such as Cu, Al, and steel, and mixtures thereof. Typical curable or thermoformable resins which may be employed to impregnate the fabric or fibrous reinforcements include phenolics, polyether ether ketones, polyimides, polyphenylene sulfides, polysulfones, polyesters, epoxies, polyethylene, polypropylene, nylon, bis-maleimides, PVC, polyamide-imides, furans, polyetherimides, ureas, urea-formaldehyde resins, melamines, polybenzimidazoles, etc., and mixtures thereof.

Computer controlled processes and systems for curing graphite resin composites are well known, and typical publications in this field include: U.S. Pat. Nos. 3,893,792; 3,925,139; 4,140,050; 4,236,109; 4,367,115; 4,373,092; 4,399,100; 4,423,191; 4,445,268; 4,449,697; 4,450,857; 4,486,996; 4,515,545; 4,559,810; 4,773,021; 4,777,431; 4,810,438; 4,828,472; 4,868,769; 5,032,525.

A number of these prior art patents involve ultrasonic detection of the composite properties during the cure process, but ultrasonic detection does not have the desired effectiveness since it is superior in detecting structural anomalies, rather than gradual changes in physical state and cure reactions.

Other patents involve the use of mathematical models, and still other patents, such as U.S. Pat. No. 4,399,100 employ dielectric sensors to determine specific curing conditions, none of which address the ongoing nature of the curing or thermoforming process itself.

Furthermore, none of the prior art patents address the question of monitoring all of the critical process events such as the onset of reaction between the initial reactants, the completion of formation of the prepolymer, the onset and termination of the cross linking reaction, the onset of melting and the completion of gelation. Consequently, these prior art patents do not adequately solve the problem of determining the most suitable time for applying heat and pressure to the curing system, and when to terminate the cure or thermoforming process.

Also, the prior art does not show how to compensate the cure conditions for variations of the partially processed composite due to variations in its formulation from different manufacturers, and for differences in thicknesses of the composite materials. The prior art also does not compensate for additional variables which are introduced into the process by the nature of the curing equipment, tooling, thermal history, etc. Another problem of the prior art is that it attempts to determine actual values of the properties undergoing processing, such as viscosity, or to determine maxima and minima of these properties. However, such actual or absolute values of properties are difficult to measure under processing conditions due to variations in geometry of the measuring sensor such as the capacitor and the constantly changing environment including electrical noise within the processing equipment.

It would be preferable to determine the characteristic shape or signature of the curve, since this would obviate the necessity of having to determine maximum or minimum values.

Moreover, the prior art utilizes sensors which are buried within the composite and these sensors detect changes in the material only in their immediate vicinity, a condition which may not be typical of the laminate as a whole. Furthermore, after completion of the cure or thermoforming process, the sensors remain in the composite as undesirable artifacts.

THE INVENTION

According to the invention, it has been found that curable and thermoformable composites produce distinctive dielectric loss response versus time curves during the cure or thermoforming process. Two components make up the total dielectric loss or impedance, viz., a resistive component and a capacitive component, and these two components are plotted separately versus time, each giving a distinctive curve. The shape of the curve is consistent, although it will vary in amplitude and time ordinate principally due to thickness, heating rate, degree of advancement and various other factors. The curve indicates distinctive process events which are characterized by PEAKS, VALLEYS, FLATS, RISES, and FALLS, which can be correlated with chemical and physical changes occurring in the composite, as it is cured or thermoformed.

Distinctive process events which are considered critical are then selected to obtain the highest quality in the finished product, but if there is uncertainty as to whether a process event is critical, this can be determined by experimentation, and will be discussed, infra. For this purpose, a dielectric loss curve having a particular distinctive shape is selected for the polymer composite being processed, and the shape of the curve is examined with a curve recognition computer program. The process cycle is divided into specific time/temperature segments and critical process events are selected within each segment. If a curve feature is not recognized, the sampling rate of the data and the sampling rate sensitivity is adjusted until the required features of the curve are invariably recognized. The above curve recognition process simulates an actual process occurring in real process equipment.

The information developed in the simulation process is then programmed into a computer for controlling the operation of the autoclave, press or other equipment used to process the composite parts. In addition, the computer actuates the various autoclave operations and performs specific cure conditions based on readings of in-situ process control monitors. The actuation timing for the applications of these specific cure conditions by the process controls is based on the specific features of the dielectric curves. In this manner, standard or fixed process signature curve features are modified or adapted at critical points to correspond with the actual condition of the material being processed.

The cure conditions which the computer is programmed to apply may include vacuum within a vacuum bag surrounding the composites, removal of volatiles, pressure (by using CO2, for example), temperature, cooling, and their respective application times, and on a real time basis. The entire system is usually run on a fully automatic computer controlled basis, but in case of sensor or equipment difficulties, the system may be run on a semi-automatic or manual basis, based on signature curve features.

DESCRIPTION OF THE PREFERRED EMBODIMENTS

Initially, it is necessary to determine critical process events in a cure cycle, and for this purpose, thermal analysis (TGA), and dynamic rheological analysis (dielectric testing) were employed during the cure process. A number of cure runs were first made to produce sample laminates, and also to produce a series of dielectric curve shapes from which were obtained a standard cure cycle curve.

The sample laminates were visually examined for defects and occasionally by ultrasonic scanning. Also, resin content, fiber volume, and void content were determined as well as flexural strength and short beam shear testing. If the results of these tests showed the cured product failed to meet product specifications, or was of poor quality, the cure cycle was modified until laminates of suitable quality were produced. A number of cure runs were made (generally, not more than two being required) to produce a series of dielectric curve shapes from which were obtained a standard cure output curve with additional sample laminates being produced.

Usually, critical process events are known to persons skilled in the art. However, to confirm that a process event is in fact critical, conditions around a particular event are varied, and if the resulting laminate is of good quality, then the particular process event is not critical. If in fact the conditions surrounding a process event are actually critical, then laminates taken from these surrounding process conditions will be inferior.

Employing this procedure, an optimized processing curve for a particular manufactured part can be made which is adjusted at critical points based on the actual condition of the part being made. Since prior experience and background data are frequently available, it may not be necessary to go through the entire procedure noted above to obtain an optimum processing curve.

Consequently, the timing of specific curing and forming events such as the removal of volatile solvents, completion of certain chemical reactions, pressure application at suitable viscosity to obtain full consolidation, and the completion of the cure or thermoforming process can be controlled, preferably by a computer.

Figure 1:
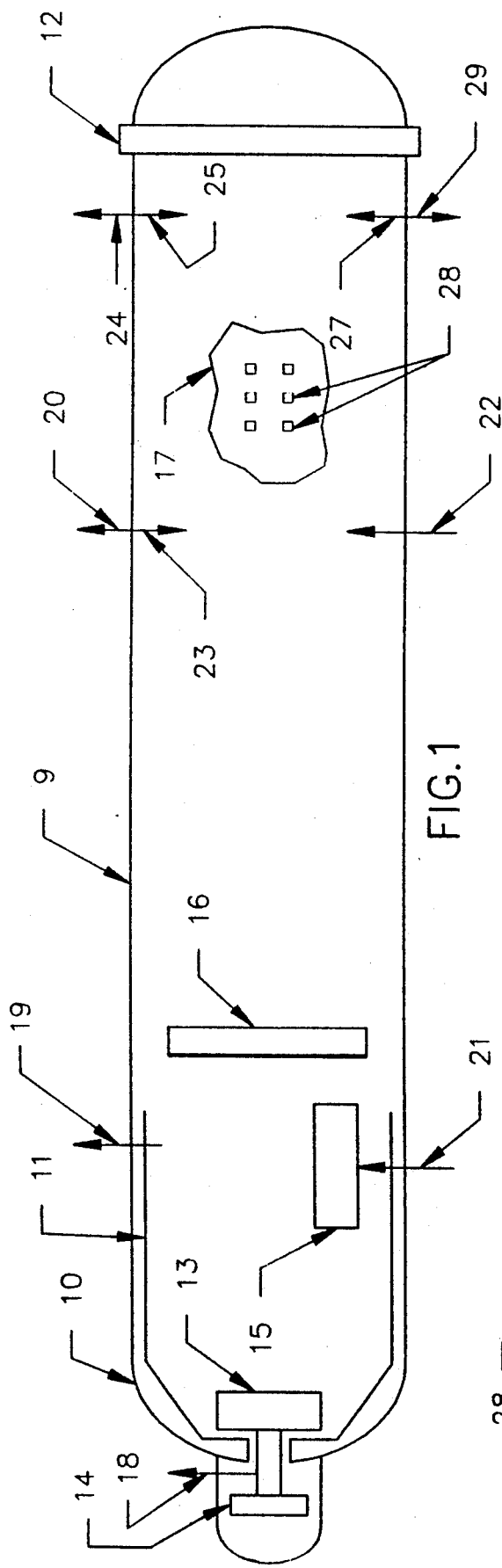
FIG. 1 is a schematic representation of an autoclave which has been modified for the computer controlled curing of laminates, according to the invention.

FIG. 1 illustrates a typical autoclave vessel 9 which may be employed for curing or thermoforming purposes, using the conditions imposed by critical process events in the process cycle. The vessel was an existing autoclave which had been modified for the curing process and was capable of operating at 850° C. and 250 psi. The autoclave has an ellipsoidal shape, and comprises an exterior vessel wall 10, and an interior insulating wall 11 enclosing a vessel interior, and a door 12 at one end of the autoclave. A blower 13 and blower motor 14 are mounted at the opposite end of the autoclave, and function to blow over heaters 15 or a cooling coil 16 and onto a composite article 17 that is being processed.

Temperature sensing elements 18, 19 and 20 are mounted within the autoclave to provide a reasonable temperature profile along the autoclave length, and temperature indicating controllers 21, 22 and 23 provide temperature control about midway of the autoclave. A pressure transducer 24 and pressure indicating controller 25 are provided to obtain pressure readings and supply pressure via say CO2, nitrogen, etc., to the autoclave. Vacuum sensing is provided by a vacuum transducer 26 along with a vacuum control 27. A plurality of dielectric sensors 28, which are described in greater detail, infra, are mounted on the exterior of the laminate and provide dielectric loss curves to indicate progress of the curing reactions, changes of physical state such as melting and solidification, changes in viscosity and other physical or chemical occurrences in the polymer. Also, temperature sensing devices such as thermocouples are located at appropriate places on the composite part and tooling.

Figure 4:
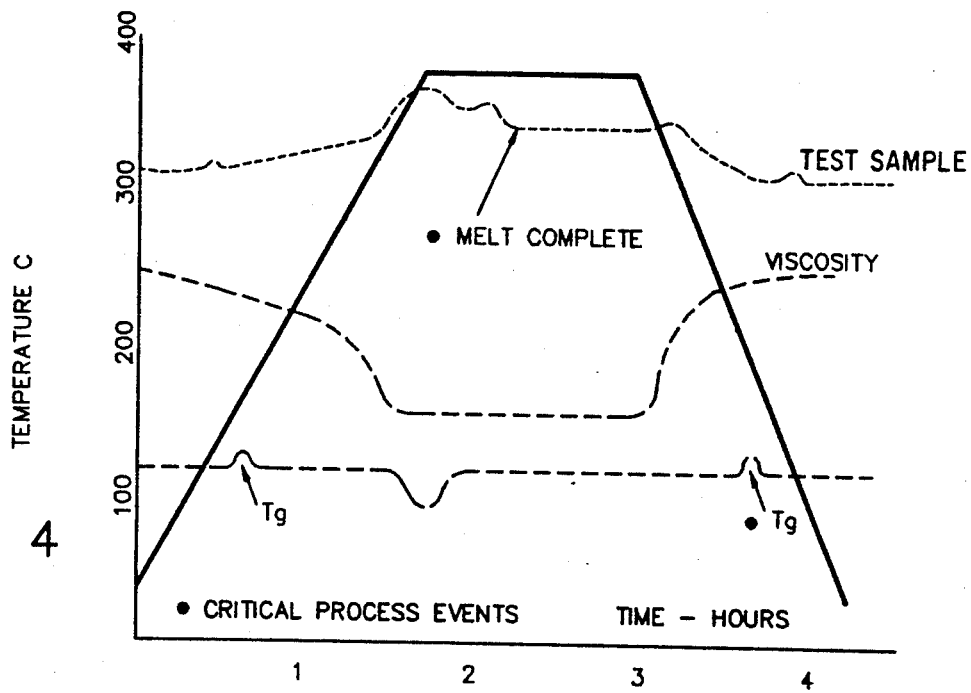
FIGS. 4, 5 and 6 are graphs showing typical temperature versus time cure profile curves, respectively for polyether ether ketone, phenolic, and polyimide composites, all impregnated into various forms of graphite cloth; and, FIG. 7 is a program useful for controlling the cure cycle of a resin impregnated laminate.
Figure 5:
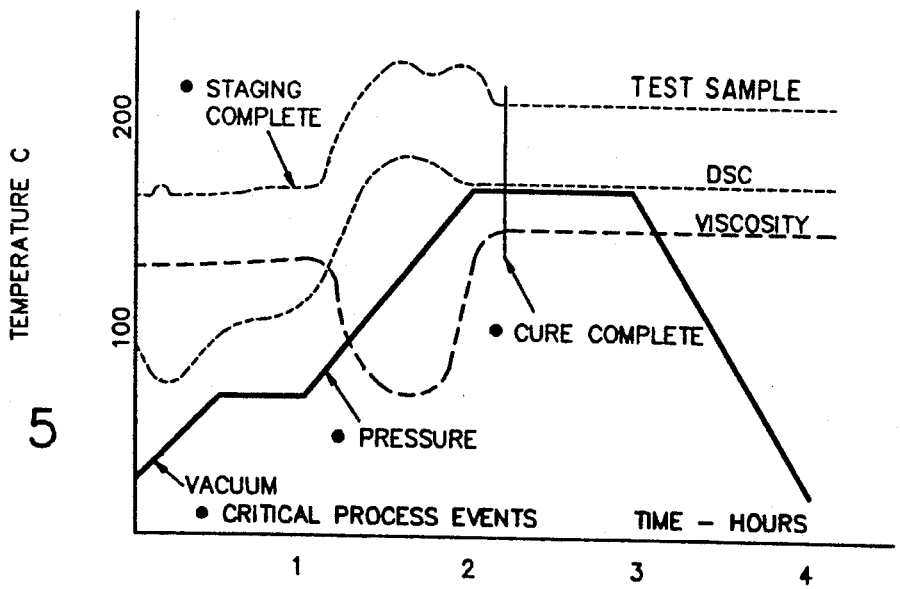
Figure 6:
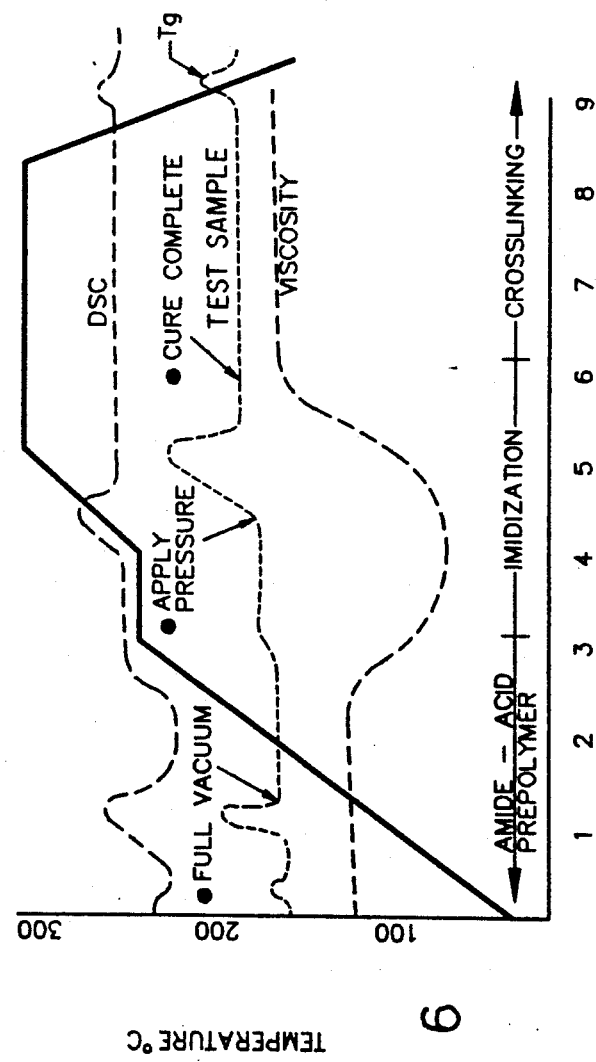

Data from all of the sensors are fed into a computer (not shown) and this data is processed for comparison with optimum cure curves (e.g., FIGS. 4, 5 and 6). Output control data is fed from the computer to the temperature controls 21, 22 and 23, the pressure control 24, and the vacuum control 27.

Figure 2:
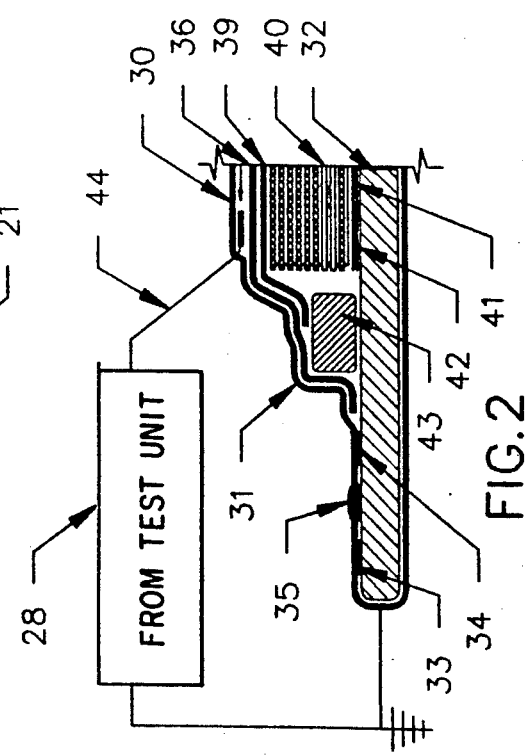
FIG. 2 is a schematic view in sectional side elevation showing the arrangement of a dielectric sensor, composite layers and lay-up components employed in fabricating a composite structure against a forming tool.

FIG. 2 illustrates a lay-up configuration 30 in a silicone based envelope bag 31, for producing a cured composite part shaped to conform with a graphite tool 32. The overall part size was 26×24 inches, and shaped as a partial frustrum typical of a structural, external airframe skin, and included flat portions, reinforcing ribs and a curved area. Graphite was selected for the tool 32 since it closely matched the coefficient of expansion of the graphite fiber reinforced composite, besides having dimensional stability, and resistance to the high temperature of the curing processes. The surface of the tool 32 was nickel plated to prevent damaging the graphite, and ten cure cycles at 385° C. produced no visible damage to the tool. The envelope bag 31 was sealed to the surface of tool 32 by means of end seals 33, 34 and a double center seal 35.

An assembly of film layers comprising breather material 36, a perforated release fabric 39, all of glass fiber, were placed on top of the composite lay-up 40. Layers of release fabric 41 and release film 42 were positioned between the composite 40 and the tool 23. At temperatures in excess of 260° C., use of polyimide film should be employed which does not exhibit dielectric activity such as ICI's polyimide UPILEX film. A dam portion 43 may be used to support the ends of envelope bag 31 and layers 36 and 39.

Figure 3:
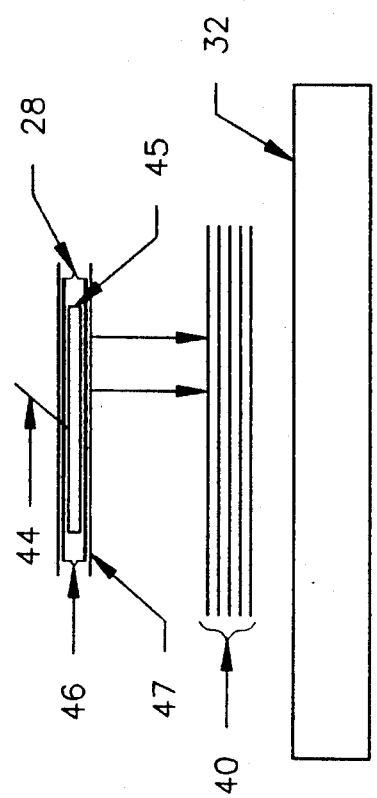
FIG. 3 is an external view of an electrode, partly cut away, and suitable for dielectric monitoring of the composite during the cure process.

The dielectric sensors 28, one sensor being shown in FIG. 3, is placed on top of the assembly of the film layers, and form a parallel plate condenser with the tool 32. This arrangement enables the electrodes to read through the laminate, compared to the action of buried electrodes which read only in the immediate vicinity of a electrode. Dielectric changes sensed during the cure process are converted to a voltage reading (e.g. 0–10 volts). A cable 44 connecting the electrode 28 is passed through the autoclave wall using a Teflon polytetrafluoroethylene pressure gland. To reduce the effects of high temperature flow of Teflon at temperatures exceeding about 550° F., the Teflon coated cable was cushioned with glass fiber cloth and over-wrapped with KAPTON polyimide film for cure temperatures in excess of about 500° F. The sensor frequency was capable of functioning at 1,000 Hz–10,000 Hz resistive signal gain and capacitive gain, and this enabled the cascading of five cascaded frequencies during a run for a given situation.

The assembled dielectric sensor 28 which was employed comprises a metal foil electrode 45 having an active area of from about $\frac{1}{2}$" square to about 1" square. Nickel electrodes are preferred to aluminum since aluminum electrodes tend to fail above say 230° C. The assembled sensor is shown in which the electrode 45 is surrounded by a suitably high temperature resistant polyimide insulating film 46 such as ICI's UPILEX material, together with an over-wrapping of insulating film 47 and bonded together with a polyimide adhesive primer. The sensor functioned up to about 750° F. When employed with phenolic cure systems, the UPILEX material tended to react with the phenolic resin, and hence the insulator was isolated from the phenolic resin with a layer of DuPont KAPTON polyimide film.

Figure 7:
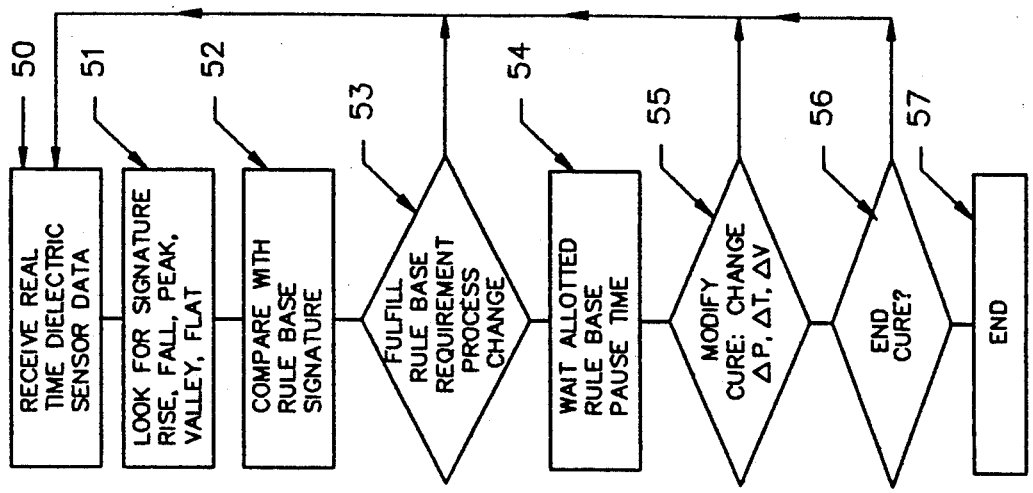

As shown in FIG. 7, a typical program for producing laminates according to the invention, comprises receiving real time sensor and dielectric data 50 from the autoclave system and the part undergoing cure. For a specific resin having a unique cure or thermoform signature 51, the computer compares 52 the real time sensor and dielectric data with the stored cure or thermoform signature and looks for a rise, fall, peak, valley or flat. If a comparison 53 with the stored signature does not fulfil a rule requirement for a process change, the program idles back in the loop 53-50 until a process change is required. However, if a process change is required, a 'rule base' allotted pause time is set 54 for the controls of the autoclave to commence functioning.

Following the requisite pause time, suitable modifications to the cure process by way of changes in temperature, pressure and vacuum are applied 55 by the autoclave controls. The program then proceeds to a feedback loop to determine if the cure has been completed 56. During this cure period, both sensor and dielectric data are fed back to the computer 50 for a signature comparison. The program continues looping between 56 and 50 until the signature comparison indicates the cure has been completed. The cure process then ends 56, the controls are turned off, and the autoclave is shut down 57.

EXAMPLE 1

A sample of polyether ether ketone (ICI's PEEK) was impregnated into ICI's AS-4 unidirectional fiber array and the results selected from a range of 1–5 MHz, are illustrated in FIG. 4.

Several plies of materials were laid up with several consolidation cycles, depending on thickness, and the temperature was raised (dark curve) until 385° C. was reached.

The critical event which was first reached was completion of melting, and the computer was programmed to recognize the well defined peak, followed by a flat and then to initiate cooling. Immediate cooling at this point not only can result in autoclave time reduction, but will reduce thermal degradation of the resin material, as compared with maintaining long process temperature hold times that are typical of the conservative prior art. It will be noted that a decrease in viscosity, indicating the onset of melting corresponded to an increase in dielectric values. A levelling off of the dielectric curve corresponds to complete melting.

Several runs were made in which the computer made the decision to initiate cooling, and the quality of the parts (described in connection with FIG. 2) were considered excellent. Ultrasonic (C scan) examination of the parts showed no significant voids, delaminations or flaws, and the properties of the thermoformed composite are given in Table 1, below.

TABLE 1

| PROPERTY | FLAT LAMINATES | DEMONSTRATION PARTS |
| --- | --- | --- |
| | (0,90)n; 16 Plies | Quasi-Isotropic; 16 Plies |
| Density | 1.5954 | 1.5695 |
| Fiber Volume | 61.5% | 63.93% |
| Void Content | 0.27% | 0.85% |
| Short Beam Shear: ASTM 234, Ult. Str. | 14,376 psi | 8,530 psi |
| 4-Point Flexure: ASTM D790 Ult. Str. | 160,406 psi | 118,366 psi |
| Modulus | 8.5 msi | 5.1 msi |

EXAMPLE 2

A sample of a phenolic composite was produced using Borden SC-1008 phenolic resin impregnated into T300, Style K135 graphite cloth sold by Ferro Corporation, and the graphic results of time versus temperature are shown in FIG. 5.

Prior art processes for curing a phenolic composite, which are used as precursors to form ablative or carbon/carbon composite structures, involve raising the temperature to about 50° C.–60° C., and maintaining that temperature range until the solvents in the system are evaporated. This temperature range is maintained until the resin is 'staged', i.e., the molecular weight has increased to a higher level, as indicated by an increase in viscosity. The temperature is then increased to 177° C. and held for about one hour or more to assure a complete cure. Full autoclave or press pressure is usually applied at some arbitrary point soon after the staging portion of the process. This prior art process cycle has been developed by trial and error, and is varied by individual operators according to the particular phenolic, and the size and thickness of the part undergoing curing.

According to the invention, it has been discovered that the dielectric loss curves showed clear indications of the critical process events which the prior art has attempted to control. For example, evaporation of solvent is indicated by a small peak, and completion of this event is indicated by a flat portion of the curve, as shown in FIG. 5. Completion of the staging process is also indicated by a flat following a gentle rise in the curve. Heating is then resumed, and as the temperature rises, a marked decrease in viscosity correlated with an increase in the Differential Scanning Calorimetry trace (DSC) occur. The increase in temperature combined with low viscosity causes a rapid increase in cross linking chemical reactions leading to gelation. Thus, two competing phenomena occur simultaneously and rapidly, resulting in a very narrow processing window. Full autoclave pressure should therefore be applied within a processing window of about two to ten minutes after this rise in the dielectric loss curve.

The application of full pressure within this narrow processing window is necessary for the preparation of a dense, void free composite. If pressure is applied too soon, the resin content of the product will be too low, but if pressure is applied too late, the product will be void filled, blistered and delaminated. Bearing in mind that the response time of the system is in the order of less than one second, there is no difficulty in applying pressure within the required time constraints.

Initially, only a partial vacuum was applied to the interior of the vacuum bag until the solvent evaporation phase was complete. After solvent evaporation, and upon completion of the 'staging' phase, a temperature increase was applied as soon as the flat portion of the curve commenced. Pressure was then applied when commencement of the rise had been observed. Completion of curing was indicated by a subsiding of a peak, which was correleated with a decrease in the Differential Scanning Calorimetry trace and an increase in viscosity. When the curve had attained a flat, cooling was commenced. Thus, all critical events were recognized and appropriate actions were taken in real time to provide an optimum cure. The process of this invention is therefore not only adaptive to the actual condition of the composite being cured but also eliminates unnecessary prolongation of various process phases, and this considerably reduces the overall process cycle.

Flat panels with and without mineral fillers, were made using the process and apparatus of this invention, and all of these panels were of excellent quality. Three demonstration parts, representing a typical airframe skin structural part, were then made with the mineral filled material, and excellent quality was again obtained. One of these parts was converted to a carbon/carbon composite with excellent results.

Test coupons were taken from the flat area of the 'as molded' demonstration parts, and the results are given in Table 2, below.

TABLE 2

| PROPERTY | DEMONSTRATION PARTS |
|---|---|
| | (0-90)n; 16 Plies |
| Density | 1.6372 |
| Fiber Volume | 45.58% |
| Void Content | **** |
| Short Beam Shear ASTM 234, Ult. Str. | 2,208 psi |
| 4-Point Flexure: ASTM D790 Ult. Str. | 23,143 psi |
| Modulus | 3.92 msi |

****Due to the proprietary nature of the inhibitor filler, the void content could not be determined. However, ultrasonic C scans of the parts showed them to be dense and of good quality.

EXAMPLE 3

Two different samples of phenolic prepregs were cured, one sample being from the Fiberite Corporation, and the other phenolic prepreg being from BASF-/NARMCO. The dielectric traces differed in amplitude, and precise timing of events of FIG. 5, but they both exhibited the typical characteristic shape of the Borden SC-1008 resin.

EXAMPLE 4

A high temperature PMR-15 polyimide resin was impregnated into T300, Style K135 graphite fiber cloth sold by the Ferro Corporation. The prepreg consisted of low molecular weight amid-acid prepolymers which increase rapidly in molecular weight in the temperature range of 80° C.-150° C. with the release of condensation products, water and methanol. These reactions continue up to 250° C. and are accompanied by imidization of the polymer with the elimination of water. Softening and melt flow of the imidized linear polymer occurs at about 175° C.-250° C. Cross linking reactions occur at about 250° C.-316° C., and FIG. 6, illustrates a general overview of the reaction. For this reason, prior art curing of PMR-15 is usually made at a maximum temperature of 330° C. for several hours to ensure a complete cure.

Using the process of this invention, the following cure procedure (dark curve - FIG. 6.) was adapted using a 5,000 Hz curve resistive loss, since it had the most distinctive shape.
1. Apply 3"-5" Hg;
2. Increase the temperature 2° C./min. until the resistive curve (viscosity) shows a fall, that can be correlated with Differential Scanning Calorimetry (DSC) which shows a rise;
3. Maintain temperature until resistive curve becomes flat;
4. Apply full vacuum - minimum 27" Hg;
5. Apply further heat until 250° C. at 2° C.-3° C. per minute;
6. Wait for the resistive curve to become very flat;
7. Apply 200 psig;
8. Increase temperature to 330° C. and wait for a fall in the resistive trace;
9. Hold at temperature for 15 minutes;
10. Cool to 204° C.;
11. Vent vacuum and release pressure gradually; and,
12. Continue cooling along the downward slope of the temperature line shown in FIG. 6, and conclude run.

Procedures 1-6 would be used for elevated temperature consolidation (debulking) if required.

Three flat panels 18"×24", and three demonstration parts as per FIG. 2 were produced, using the above described process, and all panels and parts were of excellent quality. The test results are given in Table 3, below.

TABLE 3

| PROPERTY | DEMONSTRATION PART |
|---|---|
| | (0-90)n;16 Plies |
| Density | 1.5862 |
| Fiber Volume | 61.2% |
| Void Content | less than 0.2% |
| Short Beam Shear: ASTM 234, Ult. Str. | 9,578 psi |
| 4-Point Flexure: ASTM D790 Ult. Str. | 117,855 psi |
| Modulus | 4.85 msi |

The process and apparatus of this invention enables curing conditions to be optimized while reducing the possibility of damaging the laminate due to prolonged heating, and minimizing the residence time in the autoclave. Furthermore, excellent products can be produced, even if the manufacturing sources of the raw material are different. Moreover, many existing autoclaves, presses, and ovens can be modified without great cost since they are already equipped with computer controls.

In summary, this invention insures the production of composite parts of uniform high quality, in spite of variations in raw material, pre-processing, tooling and equipment. Process cycles are significantly reduced, yields increased, and the technique applies an excellent quality control record of the process for each part. Past inspection operations which were normally intensively used to assure the quality of the part, may now be drastically reduced or eliminated.

We claim:

1. A process for curing or thermoforming a resin with a fiber fabric or filler reinforcement to form a composite, comprising:
   a.) measuring curing or thermoforming conditions by dielectric means applied on opposite sides and through the composite, during the cure or thermoforming process to produce a process curve for a specific resin which is correlated with physical and chemical changes in the resin;
   b.) comparing the process curve for the specific resin with a signature curve defining peaks, valleys, flats, rises and falls which are correlated with physical and chemical changes in the resin and fabric, the comparison being made at critical process events along the curves which are critical to the curing or thermoforming reaction; and,
   c.) applying reaction conditions in real time to the resin and fabric to conform the process curve with the signature curve, including the said critical process events, to form the composite, the composite having fewer voids and improved and uniform quality, and the process resulting increased yields and reduced process cycle time.

2. The process of claim 1, in which the physical and chemical changes in the resin and fabric are measured by differential scanning calorimetry, determined through measurement of viscosity and determined through measurement of glass transition temperature.

3. The process of claim 1, in which the reaction conditions applied include: vacuum to remove volatile solvents, venting and variations in temperature and pressure, and the critical process events include release of volatiles, the onset of reaction between initial reactants, prepolymer formation, onset and termination of cross linking, onset of melting and complete solidification.

4. The process of claim 1, in which the dielectric measurements include resistance loss and capacitance loss.

5. The process of claim 1, in which the critical process events are determined by thermal analysis, rheological analysis and dielectric measurements.

6. The process of claim 4, in which the dielectric measurements are made at a sensor frequency of about 1,000 Hz–10,000 Hz.

7. The process of claim 1, in which the said resin is selected from the group consisting of: phenolics, polyether ether ketones, polyimides, polyphenylene sulfides, polyesters, polysulfones, epoxies, polyethylene, polypropylene, nylon, bis-maleimides, PVC, polyamide-imides, urea-formaldehyde, furans, melamines, polyetherimides, ureas, polybenzimidazoles, and mixtures thereof.

8. The process of claim 7, in which the said fabric or filler reinforcement consists of: carbon black, graphite, glass fiber, quartz, SiC, aramid, metal fibers, Cu, Al, steel, or mixtures thereof.

9. The process of claim 1, in which the said process is controlled by means including computer, semi-automatic or on a manual basis.

10. The process of claim 1, in which the resin, composite and dielectric means are contained in a silicone bag.

11. The process of claim 1, in which the fabric is carbon fiber and the resin is polyether ether ketone.

12. The process of claim 1, in which the fabric is carbon fiber and the resin is a polyimide.

13. The process of claim 1, in which the fabric is carbon fiber and the resin is a phenolic.

14. The process of claim 1, in which the fabric is carbon fiber and the resin is an epoxy.

15. The process of claim 1, in which the fabric is carbon fiber and the resin is a bis-maleimide.

16. The process of claim 1, in which the fabric is carbon fiber and the resin is a polysulfone.

17. The process of claim 1, in which the fabric is carbon fiber and the resin is a polyphenylene sulfide.

18. The process of claim 9, in which the computer has a response time in the order of less than one second.

19. The process of claim 1, in which the composite is formed on a tool, and the dielectric means includes the tool.

20. A process for curing or thermoforming a resin with a fiber fabric or filler reinforcement to form a composite, comprising:
   a.) measuring curing or thermoforming conditions by dielectric means applied on opposite sides and through the composite, during the cure or thermoforming process to produce a process curve for a specific resin which is correlated with physical and chemical changes in the resin;
   b.) comparing the process curve for the specific resin with a signature curve which is characteristic of the resin or composite being processed and which is correlated with physical changes in the resin and fabric, the comparison being made at critical process events along the signature curve which are critical to the curing or thermoforming reaction; and,
   c.) applying reaction conditions in real time to the resin and fabric to conform the process curve with the signature curve, including the said critical process events, to form the composite, the composite having fewer voids and improved and uniform quality and the process resulting in increased yields and reduced process cycle time.

21. The process of claim 20, in which the composite is formed on a tool, and the dielectric means includes the tool.

* * * * *